US012751731B2

(12) United States Patent
Lao et al.

(10) Patent No.: US 12,751,731 B2
(45) Date of Patent: Oct. 6, 2026

(54) ANTI-BREAKAGE SELF-LOCKING UNIVERSAL SURGICAL CLAMP

(71) Applicant: Guangzhou Aquila Precise Tools Limited, Guangzhou (CN)

(72) Inventors: Shen Lao, Guangzhou (CN); Jianxing He, Guangzhou (CN); Jun Liu, Guangzhou (CN); Wei Wang, Guangzhou (CN); Hengrui Liang, Guangzhou (CN); Hao Chen, Guangzhou (CN); Qingyang Hu, Guangzhou (CN); Qiang Deng, Guangzhou (CN); Ziyang Chen, Guangzhou (CN)

(73) Assignee: Guangzhou Aquila Precise Tools Limited, Guangzhou (CN)

( * ) Notice: Subject to any disclaimer, the term of this patent is extended or adjusted under 35 U.S.C. 154(b) by 0 days.

(21) Appl. No.: 19/231,380

(22) Filed: Jun. 6, 2025

(65) Prior Publication Data

US 2026/0165723 A1 Jun. 18, 2026

(30) Foreign Application Priority Data

Dec. 17, 2024 (CN) ......................... 202411858940.4

(51) Int. Cl.
*A61B 17/28* (2006.01)
*A61B 17/00* (2006.01)

(52) U.S. Cl.
CPC ............................... *A61B 17/2833* (2013.01); *A61B 2017/00867* (2013.01); *A61B 2017/2845* (2013.01)

(58) Field of Classification Search
CPC .. A61B 2017/00367; A61B 2017/2929; A61B 2017/2845; A61B 2017/2946;
(Continued)

(56) References Cited

U.S. PATENT DOCUMENTS 5,626,608 A * 5/1997 Cuny ................. A61B 17/2909
606/205
5,984,939 A * 11/1999 Yoon .................. A61B 18/1442
606/205

(Continued)

FOREIGN PATENT DOCUMENTS

CN 105796147 A 7/2016
CN 109199519 A 1/2019
CN 109219402 A 1/2019

*Primary Examiner* — Sarah A Long
*Assistant Examiner* — Lauren Dubose
(74) *Attorney, Agent, or Firm* — Nitin Kaushik

(57) ABSTRACT

An anti-breakage self-locking universal surgical clamp is provided, which includes a handle body, a hook, a first nickel titanium wire rope, a front handle, and a clamp head. An inner wall side of the handle body is fixedly provided with a first positioning screw, and an outer wall side of the handle body is movably provided with the front handle. An outer wall side of the handle body is movably provided with the clamp head, the inner wall side of the handle body is fixedly provided with the hook. An outer wall side of the first positioning screw is fixedly provided with a first tension spring, which is connected to the hook through a head tension hook. The present disclosure achieves opening and closing function of surgical clamp by the front handle, the first nickel titanium wire rope, and a return spring.

10 Claims, 13 Drawing Sheets

(58) Field of Classification Search
CPC ........... A61B 2017/00424; A61B 2017/00526; A61B 2017/2837; A61B 2017/2925; A61B 2017/2927; A61B 2017/292; A61B 17/2909; A61B 17/2833; A61B 17/29; A61B 17/28; A61B 17/2841; A61B 17/00; A61B 17/00234; A61B 18/1445
See application file for complete search history.

(56) References Cited

U.S. PATENT DOCUMENTS

| | | | | |
|---|---|---|---|---|
| 2006/0206144 | A1* | 9/2006 | Miersch | A61B 17/2909 606/205 |
| 2007/0299469 | A1* | 12/2007 | Carpenter | A61B 17/2909 606/205 |
| 2008/0255608 | A1* | 10/2008 | Hinman | A61B 17/29 606/205 |
| 2011/0009850 | A1* | 1/2011 | Main | A61B 17/2909 606/1 |
| 2012/0296371 | A1* | 11/2012 | Kappus | A61B 17/295 606/205 |
| 2019/0298440 | A1* | 10/2019 | Mensch | A61B 17/2909 |
| 2020/0289141 | A1* | 9/2020 | Yuan | A61B 17/2909 |
| 2020/0315692 | A1* | 10/2020 | Schneider | A61B 18/1206 |

* cited by examiner

ANTI-BREAKAGE SELF-LOCKING UNIVERSAL SURGICAL CLAMP

CROSS-REFERENCE TO RELATED APPLICATIONS

This application claims priority to Chinese Patent Application No. 202411858940.4, filed on Dec. 17, 2024, which is hereby incorporated by reference in its entirety.

TECHNICAL FIELD

The present disclosure relates to the field of medical device technologies, and in particular, to an anti-breakage self-locking universal surgical clamp.

BACKGROUND

Surgical universal forceps are an important tool widely used in surgical procedures, aimed at providing doctors with higher flexibility and precision in surgical operations. Its design goal is to assist surgeons in easily adjusting and fixing surgical instruments or tissue clamps within limited operating space, especially in complex or narrow anatomical areas. Traditional fixed pliers are easily limited by space and angle limitation during operation, and universal pliers achieve multi-angle and multi-directional free adjustment through their special structure.

With the increasing demand for minimally invasive and complex surgeries, the innovative design of surgical universal forceps is also increasingly focused on providing more precise control and rapid adjustment while ensuring operational stability. This tool not only improves the doctor's operational freedom, but also significantly enhances the efficiency and safety of surgery.

CN115644997B discloses a universal adjustable surgical instrument, which achieves the accuracy of universal adjustment of surgical clamp during surgery, improves surgical efficiency and ensures the success rate of surgery. However, this surgical instrument cannot achieve the opening and closing function of surgical clamp.

CN116492021B discloses a surgical instrument head, which realizes the universal turning of the clamp assembly. It is not only easy to operate but also enables precise control of the surgical instrument head. However, this surgical instrument head cannot achieve the unloading and anti-breakage function of a surgical clamp.

CN109172058B discloses an acetabular cup fixed screw clamping forceps. Which realizes easier engagement of the universal screwdriver head and screw through a guiding structure, thereby facilitating surgical operations. However, the clamping forceps cannot achieve rotation and swinging functions of the surgical clamp.

CN102008341B discloses universal medical forceps, which achieves reasonable structural design, good effect, and convenient and safe surgical use. However, the universal medical forceps cannot achieve the self-locking function of surgical clamp.

In summary, the above-mentioned device cannot achieve the opening and closing function of surgical clamp, the unloading and anti-breakage function of surgical clamp, the rotation and swinging function of surgical clamp, and the self-locking function of surgical clamp, resulting in complex surgical operations, multiple patient wounds, slow recovery speed, easy postoperative infection, and poor convenience of use.

Therefore, a surgical universal clamp with anti-breakage and self-locking function that can achieve opening and closing function of surgical clamp, unloading and anti-breakage function of surgical clamp, rotation and swinging function of surgical clamp, and the self-locking function of surgical clamp is provided.

SUMMARY

The purpose of the present disclosure is to provide an anti-breakage self-locking universal surgical clamp, in order to solve technical problems of complex surgical operations, multiple patient incisions, slow recovery speed, easy post-operative infection, and poor usability caused by an inability to achieve opening and closing function, force unloading and anti-breakage function, rotation and swing function, and self-locking function of the surgical clamp proposed in the background technology.

To achieve the above objectives, the present disclosure provides the following technical solution: an anti-breakage self-locking universal surgical clamp, including a handle body, a hook, a first nickel titanium wire rope, a front handle, and a clamp head, where an inner wall side of the handle body is fixedly provided with a first positioning screw, an outer wall side of the handle body is movably provided with the front handle, an outer wall side of the handle body is movably provided with the clamp head, the inner wall side of the handle body is fixedly provided with the hook, an outer wall side of the first positioning screw is fixedly provided with a first tension spring, and the first tension spring is connected to the hook through a first head tension hook, the hook is fixedly provided on the inner wall side of the handle body, one side of the hook is fixedly provided with a positioning column, and an unlocking button is fixedly provided in a middle of the hook; a second positioning screw is fixedly provided on the inner wall side of the handle body, a second tension spring is sleeved on an outer wall side of the second positioning screw; the second tension spring is connected to a hanging hole provided on a middle side of the front handle through a second head tension hook; a first shaft sleeve is fixedly provided on a middle outer wall side of the front handle, and a first rotating shaft is movably provided in a middle of the first shaft sleeve; a positioning sleeve is fixedly provided on an upper end of the front handle, the positioning sleeve is riveted together with the first nickel titanium wire rope, a transmission wheel is fixedly provided on the inner wall side of the handle body; the first nickel titanium wire rope is connected to the clamp head around the transmission wheel, the transmission wheel is movably provided on an unloading device; a front end of the handle body is fixedly provided with a connecting sleeve, and the connecting sleeve is connected to a second rotating device through threads; the unloading device and a first rotating device are movably provided in the handle body; an outer wall side of the front handle is fixedly provided with a lock buckle, and the lock buckle is fixed by a screw that is fixedly provided at a bottom of an inner wall of the front handle.

In some embodiments of the present disclosure, the unloading device is provided in the handle body, one side of the handle body is fixedly provided with an unloading shell, and a second positioning pin is provided in the unloading shell, a movable shaft is movably provided on an outer wall side of the unloading shell, an unloading spring is fixedly provided in a middle of the movable shaft, and an adjustment nut is fixedly provided on an outer wall side of a tail end of the movable shaft to adjust a maximum force subjected by the surgical clamp; a front end of the movable shaft is fixedly provided with the transmission wheel, a second rotating shaft is fixedly provided on an outer wall side of the transmission wheel.

In some embodiments of the present disclosure, the handle body is installed with a first connecting shaft in the second rotating device together through the connecting sleeve, a rubber pad and a rotating component are fixedly provided on an inner wall side of the first connecting shaft; a copper sleeve and a threaded sleeve are fixedly provided at a tail end of the first connecting shaft, a limit pin is fixedly provided below an end face of the rotating component; a spring and a positioning steel ball are fixedly provided above the rotating component, a threaded part of the rotating component is fixedly provided with a rod sleeve, and the rod sleeve is connected to the rotating component through threads; a surface of the rod sleeve is sleeved with a rotating handle, a flushing port is fixedly provided at a front hole position of the rotating handle, the flushing port is connected to the rod sleeve and the rotating handle together through threads; an inner wall of the connecting sleeve is provided with a fixing screw.

In some embodiments of the present disclosure, an outer wall side of the rod sleeve in the second rotating device is fixedly provided with a rod body through an outer tube, a second connecting shaft is fixedly provided in the outer tube, an interior of the second connecting shaft is fixedly sleeved with a rope rod, a connector is fixedly provided at a front end of the outer tube, and the connector is connected to a swinging structure together; the first rotating device is fixedly provided on a surface of a tail end of the second connecting shaft, and a second shaft sleeve is configured to fix the first rotating device inside the second connecting shaft.

In some embodiments of the present disclosure, the first rotating device is provided with the rod body in the handle body together, a transmission shaft is fixedly provided on a surface of the second connecting shaft, a surface of the transmission shaft is fixedly sleeved with a rotating sleeve, and transmission pins are provided in two small holes in a middle of the rotating sleeve, the transmission pins cooperate with a spiral groove that is provided in a middle of the transmission shaft.

In some embodiments of the present disclosure, the connector is fixedly connected to a swing arm body through a third connecting pin, the other end of the swing arm body is fixedly installed with a connecting piece together, and is movably connected with a first connecting pin; the other end of the connecting piece is installed with the second connecting shaft in the rod body together, and is movably connected with a second connecting pin.

In some embodiments of the present disclosure, a front end of the clamp head is fixedly provided with an upper head and a lower head, transmission plates are respectively provided in inner wall sides of the upper head and the lower head, and the transmission plates are connected by first positioning pins, other ends of the transmission plates are fixedly connected to a transmission pin shaft, and the transmission pin shaft is installed on the swing arm body.

In some embodiments of the present disclosure, a second nickel titanium wire rope is provided in a middle of the transmission pin shaft, and a return spring is sleeved on a surface of the second nickel titanium wire rope, the return spring is provided in a groove of the swing arm body.

In some embodiments of the present disclosure, the upper head and the lower head are merged and installed on the swing arm body, the upper head and the lower head are fixedly connected with a fourth connecting pin.

In some embodiments of the present disclosure, a surface the rotating sleeve is fixedly provided with a rotating wheel, a tail end of the transmission shaft is fixedly provided with a sliding groove, one side of the handle body is provided with a central column, and the central column is fastened to one side of the handle body through an interference fit, a surface of the central column is provided with a reset spring, an upper end of the reset spring is provided with the hook, an upper of the hook is provided with the unlocking button, a circular hole on one side of the unlocking button is provided with a locking pin, and the locking pin is fixed above the unlocking button by welding.

Compared with the existing technology, the beneficial effects of the present disclosure are as follows.

1. The present disclosure achieves the opening and closing function of surgical clamp by providing the front handle, the first nickel titanium wire rope, and the return spring. Through universal design, it accurately clamps and cleans lymph nodes at different positions, making up for limitations of traditional surgical treatment of thoracic surgical diseases and expanding the scope of surgical indications.

2. The present disclosure achieves the unloading and anti-breakage function of surgical clamp by providing the unloading shell, unloading spring, and transmission wheel, ensuring minimal surgical trauma, low infection rate, and fast body recovery, realizing medical technology innovation and development, and providing valuable experience for subsequent medical research and development.

3. The present disclosure achieves the rotation and swinging functions of surgical clamp by providing rotating components, rotating handles, rotating wheels, and transmission pins. While continuing the advantages of minimally invasive surgery, it further reduces the number and size of surgical incisions, minimizes patient trauma, reduces postoperative complications, and promotes the overall recovery process of patients.

4. The present disclosure achieves the self-locking function of surgical clamp by providing the lock buckle, reset spring, and hook, thereby solving a problem of complex operation procedures and inability to free hands caused by the inability of surgical clamp to self-lock, and thereby improving the convenience of using surgical clamp.

Figure 1:
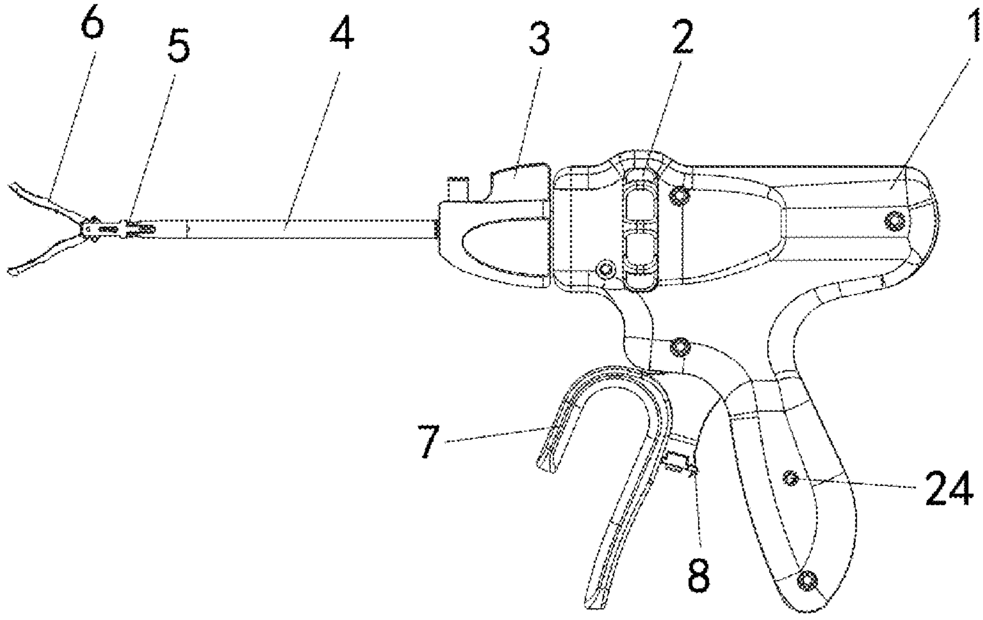
FIG. 1 is a schematic diagram of a front structure of the present disclosure.
Figure 2:
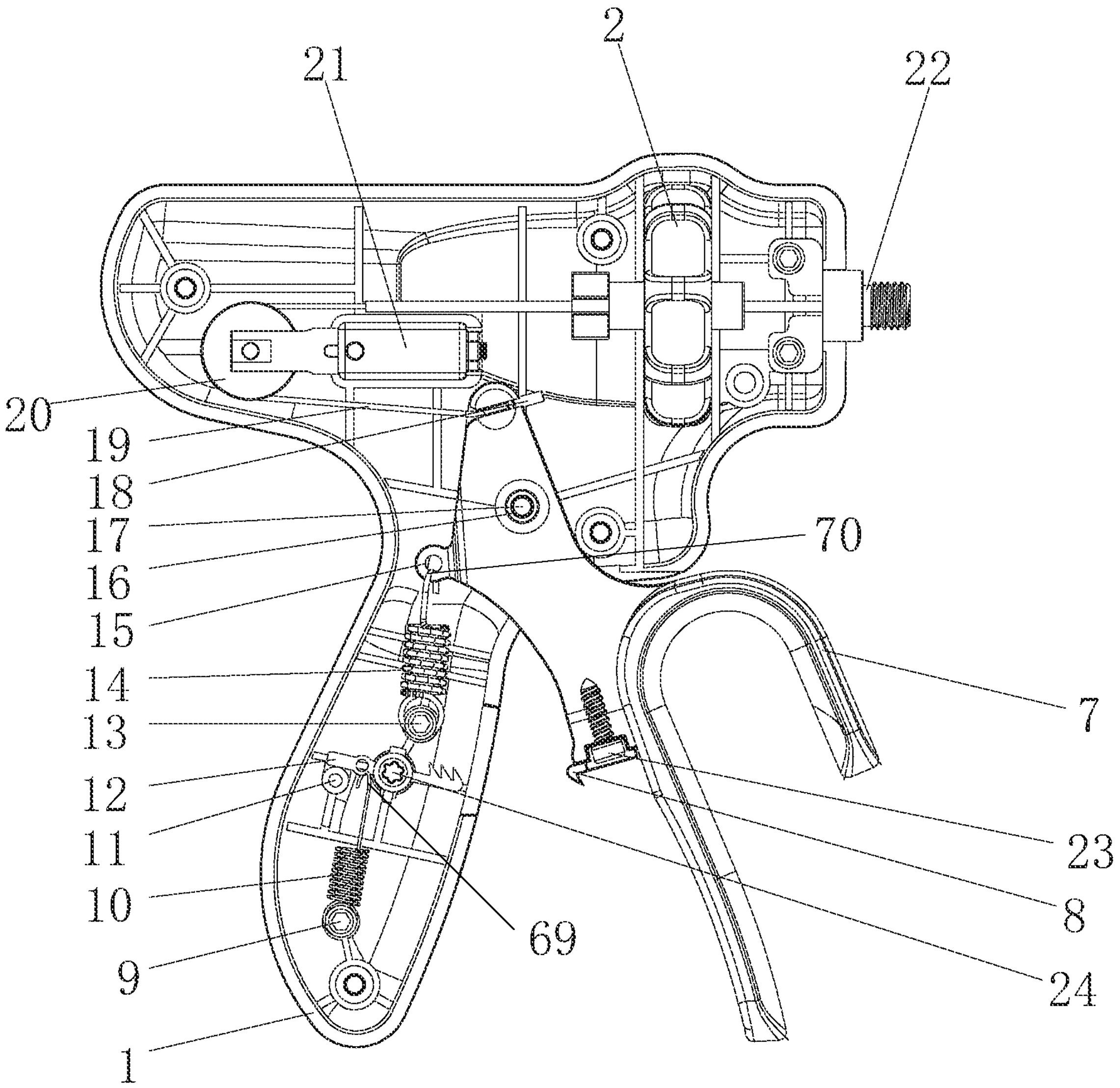
FIG. 2 is a partial schematic diagram of the front structure of the present disclosure.
Figure 3:
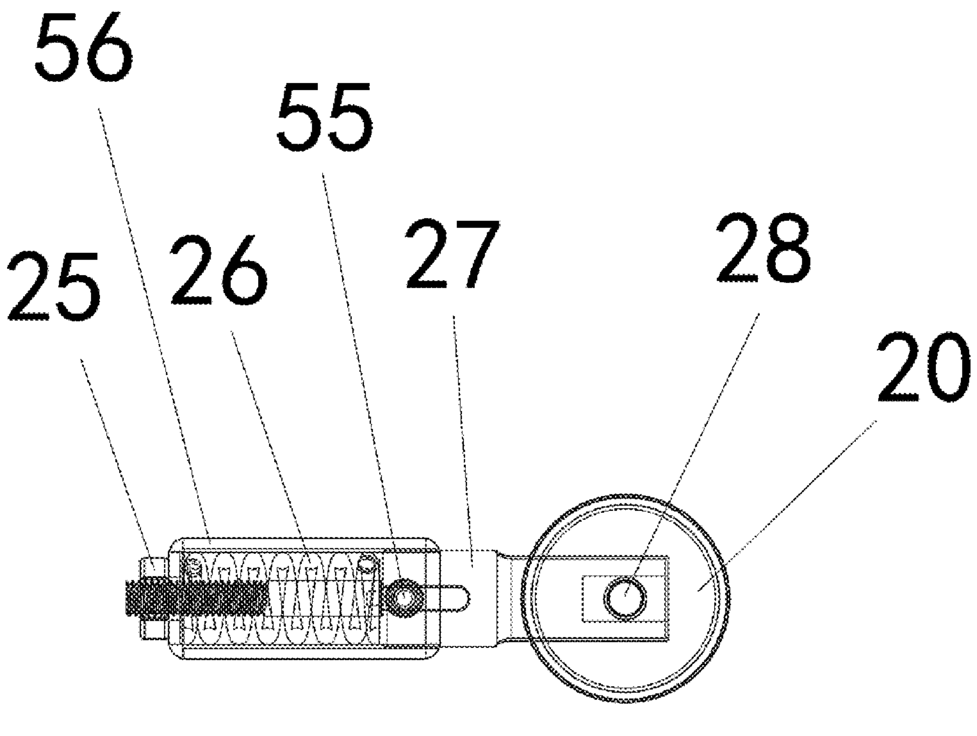
FIG. 3 is a schematic structural diagram of a movable shaft of the present disclosure.

Numeral reference: 1. handle body; 2. first rotating device; 3. second rotating device; 4. rod body; 5. swinging structure; 6. clamp head; 7. front handle; 8. lock buckle; 9. first positioning screw; 10. first tension spring; 11. positioning column; 12. hook; 13. second positioning screw; 14. second tension spring; 15. hanging hole; 16. first shaft sleeve; 17. first rotating shaft; 18. positioning sleeve; 19. first nickel titanium wire rope; 20. transmission wheel; 21. unloading device; 22. connecting sleeve; 23. screw; 24. unlocking button; 25. adjustment nut; 26. unloading spring; 27. movable shaft; 28. second rotating shaft; 29. rod sleeve; 30. flushing port; 31. rotating handle; 32. first connecting shaft; 33. connector; 34. outer tube; 35. second connecting shaft; 36. rope rod; 37. transmission shaft; 38. rotating wheel; 39. rotating sleeve; 40. sliding groove; 41. transmission pin; 42. swing arm body; 43. first connecting pin; 44. connecting piece; 45. second connecting pin; 46. third connecting pin; 47. upper head; 48. first positioning pin; 49. transmission plate; 50. return spring; 51—transmission pin shaft; 52. fourth connecting pin; 53. lower head; 54. second nickel titanium wire rope; 55. second positioning pin; 56. unloading shell; 57. rubber pad; 58. copper sleeve; 59. threaded sleeve; 60. rotating component; 61. limit pin; 62. spring; 63. positioning steel ball; 64. second shaft sleeve; 65. fixing screw; 66. locking pin; 67. reset spring; 68. central column; 69. first head tension hook; 70. second head tension hook.

DETAILED DESCRIPTION OF THE EMBODIMENTS

Below, the technical solutions in the embodiments of the present disclosure will be clearly and completely described in combination with the accompanying drawings. Obviously, the described embodiments are only a part of the embodiments of the present disclosure, not all of them. Based on the embodiments of the present disclosure, all other embodiments obtained by those skilled in the art without creative work are within the protection scope of the present disclosure.

In a description of the present disclosure, it should be noted that terms "up", "down", "inside", "outside", "front end", "back end", "two ends", "one end", "the other end", etc. indicate orientation or positional relationships based on the orientation or positional relationships shown in the accompanying drawings, only for a convenience of describing the present disclosure and simplifying the description, and do not indicate or imply that the device or element referred to must have a specific orientation, be constructed and operated in a specific orientation, and therefore cannot be understood as a limitation of the present disclosure. Besides that, terms "first" and "second" are only used for descriptive purposes and cannot be understood as indicating or implying relative importance.

In the description of the present disclosure, it should be noted that unless otherwise specified and limited, terms "installation", "provided", "connection with", etc. should be broadly understood. For example, "connection" can be a fixed connection, a detachable connection, or an integral connection; it can be a mechanical connection or an electrical connection; it can be directly connected, indirectly connected through an intermediate medium, or connected internally between two components. For those skilled in the art, specific meanings of the above terms in the present disclosure can be understood according to a specific situation.

Please refer to FIGS. 1, 2, 3, and 9. An embodiment of the present disclosure provides an anti-breakage self-locking universal surgical clamp, including a handle body 1, a hook 12, a first nickel titanium wire rope 19, a front handle 7, and a clamp head 6. An inner wall side of the handle body 1 is fixedly provided with a first positioning screw 9, an outer wall side of the handle body 1 is movably provided with the front handle 7, the outer wall side of the handle body 1 is movably provided with the clamp head 6. The inner wall side of the handle body 1 is fixedly provided with the hook 12, and an outer wall side of the first positioning screw 9 is fixedly provided with a first tension spring 10. The first tension spring 10 is connected to the hook 12 together through a first head tension hook 69. The hook 12 is fixedly provided on the inner wall side of the handle body 1. One end of the hook 12 is fixedly provided with a positioning column 11, and a middle of the hook 12 is fixedly provided with an unlocking button 24. The inner wall side of the handle body 1 is fixedly provided with a second positioning screw 13, and an outer wall of the second positioning screw 13 is sleeved with a second tension spring 14. The second tension spring 14 is connected to a hanging hole 15 that is provided on a middle side of the front handle 7 through a second head tension hook 70. A first shaft sleeve 16 is fixedly provided on a middle outer wall side of the front handle 7, and a first rotating shaft 17 is movably provided in a middle of the first shaft sleeve 16. An upper end of the front handle 7 is fixedly provided with a positioning sleeve 18, and the positioning sleeve 18 is riveted to the first nickel titanium wire rope 19. The inner wall side of the handle body 1 is fixedly provided with a transmission wheel 20, and the first nickel titanium wire rope 19 is wound around the transmission wheel 20 and is connected to the clamp head 6. The transmission wheel 20 is movably provided on an unloading device 21, and a front end of the handle body 1 is fixedly provided with a connecting sleeve 22, and the connecting sleeve 22 is connected to the second rotating device 3 through threads. An interior of the handle body 1 is provided with the unloading device 21 and a first rotating device 2. An outer wall side of the front handle 7 is fixedly provided with a lock buckle 8, and the lock buckle 8 is fixed by a screw 23 that is provided at a bottom inner wall of the front handle 7.

A front end of the clamp head 6 is fixedly provided with an upper head 47 and a lower head 53. Inner wall sides of the upper head 47 and the lower head 53 are respectively provided with transmission plates 49, which are connected by a first positioning pin 48. Other ends of the transmission plates 49 are fixedly connected to a transmission pin shaft 51, and the transmission pin shaft 51 is provided on a swing arm body 42.

A middle of the transmission pin shaft 51 is provided with a second nickel titanium wire rope 54, and a surface of the second nickel titanium wire rope 54 is sleeved with a return spring 50, and the return spring 50 is provided in a groove of the swing arm body 42.

The upper head 47 and the lower head 53 are merged together and then installed on the swing arm body 42. The upper head 47 and the lower head 53 are fixedly connected through a fourth connecting pin 52.

In an implementation mode, the upper head 47 and the lower head 53 are merged together and then installed through the fourth connecting pin 52. The upper head 47 and the lower head 53 are respectively provided with the transmission plates 49, and the first positioning pin 48 is welded to the upper head 47 and the lower head 53 after passing through holes of the transmission plates 49. Other ends of the transmission plates 49 are provided with the transmission pin shaft 51, and the middle of the transmission pin shaft 51 is connected to the second nickel titanium wire rope 54. The surface of the second nickel titanium wire rope 54 is provided with the return spring 50. The second nickel titanium wire rope 54 is riveted to a rope rod 36, and the other end of the rope rod 36 is riveted to the first nickel titanium wire rope 19. The first nickel titanium wire rope 19 is wound around the transmission wheel 20 and connected to the front handle 7. A tail end of the first nickel titanium wire rope 19 is riveted together with the positioning sleeve 18. The positioning sleeve 18 is fastened into a groove of the front handle 7.

When the front handle 7 is closed, the front handle 7 is moved around the first rotating shaft 17. The front handle 7 pulls the first nickel titanium wire rope 19, and the rope rod 36 and the second nickel titanium wire rope 54 are driven to move together. The second nickel titanium wire rope 54 pulls the transmission pin shaft 51, and the transmission pin shaft 51 pulls the transmission plates 49 to move. The transmission plates 49 pull the upper head 47 and the lower head 53 to close. When the handle is released, the return spring 50 pushes the transmission pin shaft 51 back to its original position, the upper head 47 and the lower head 53 are in an open state again. The second tension spring 14 pulls the front handle 7 back to its original position, thereby achieving opening and closing function of the surgical clamp.

Figure 4:
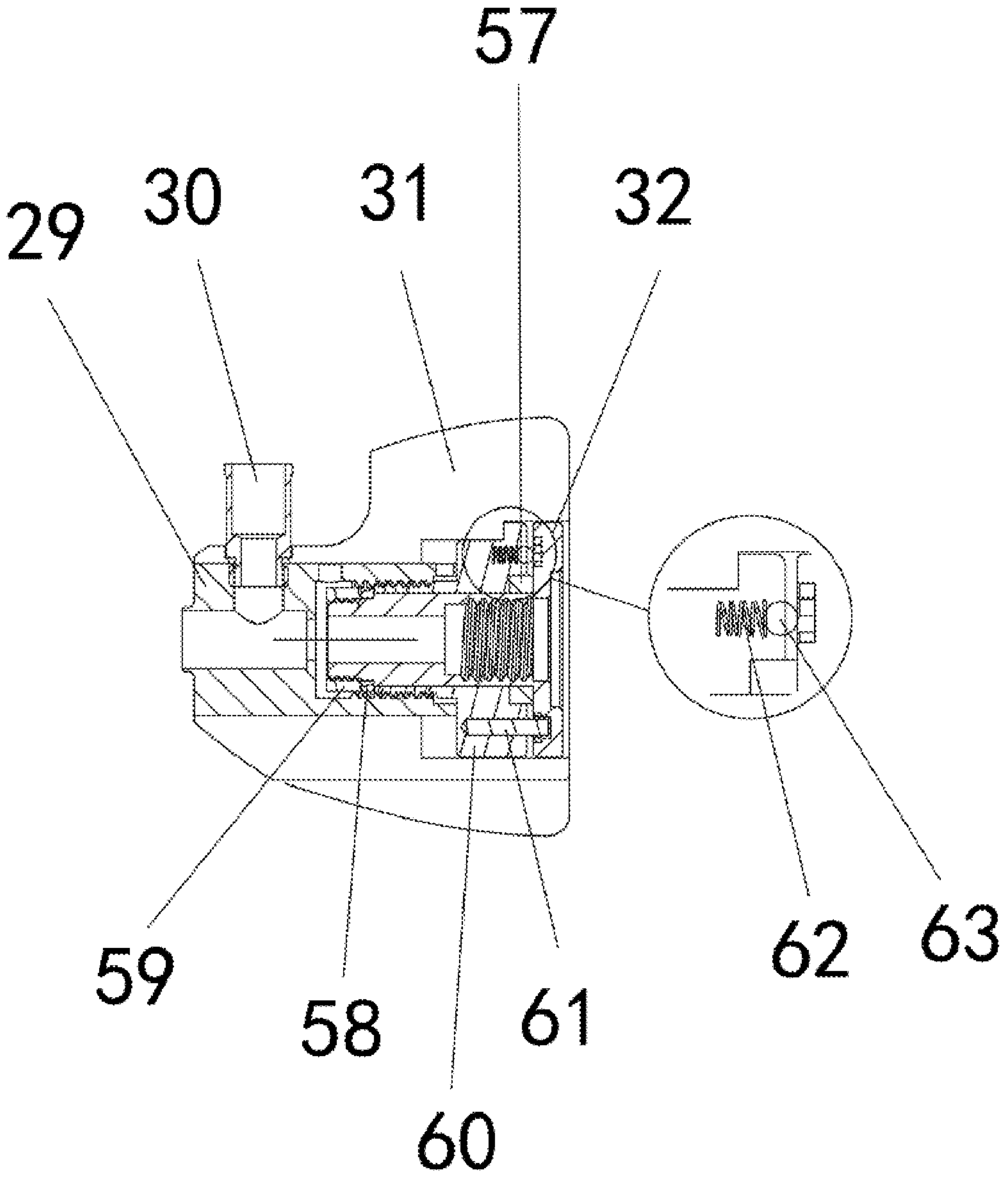
FIG. 4 is a schematic structural diagram of a first connecting shaft of the present disclosure.
Figure 5:
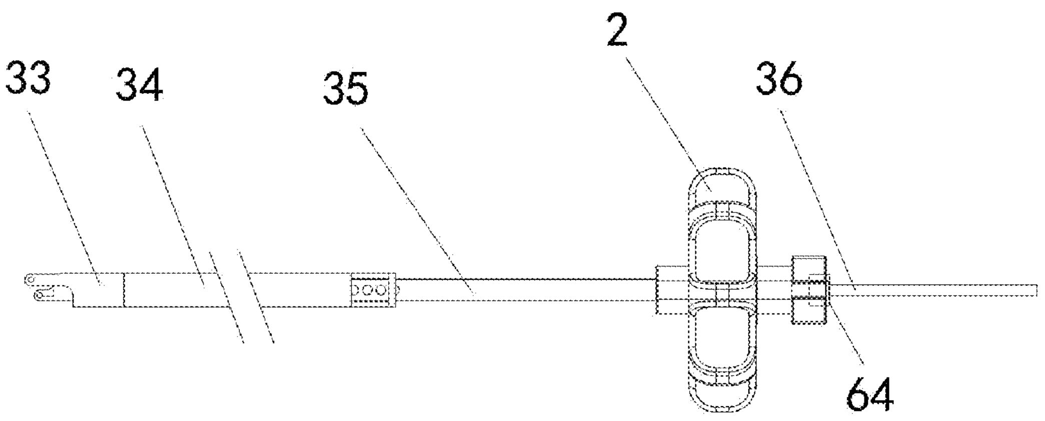
FIG. 5 is a schematic structural diagram of a second connecting shaft of the present disclosure.
Figure 6:
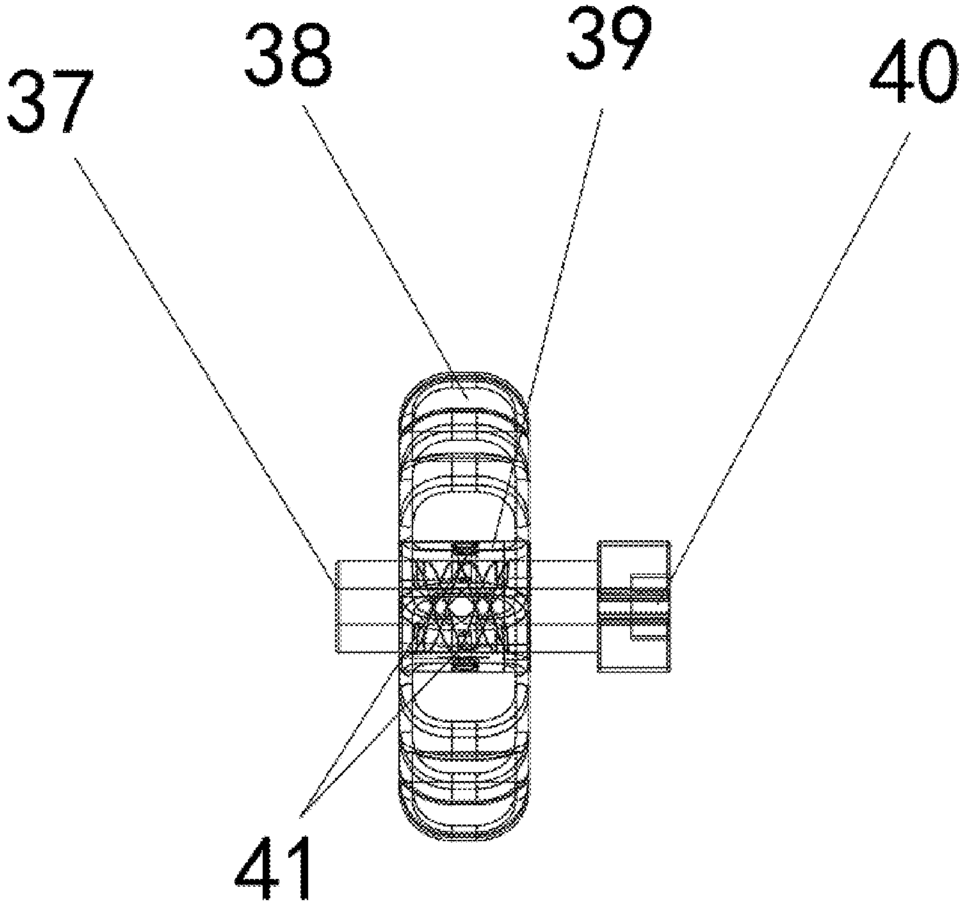
FIG. 6 is a schematic structural diagram of a transmission shaft of the present disclosure.
Figure 10:
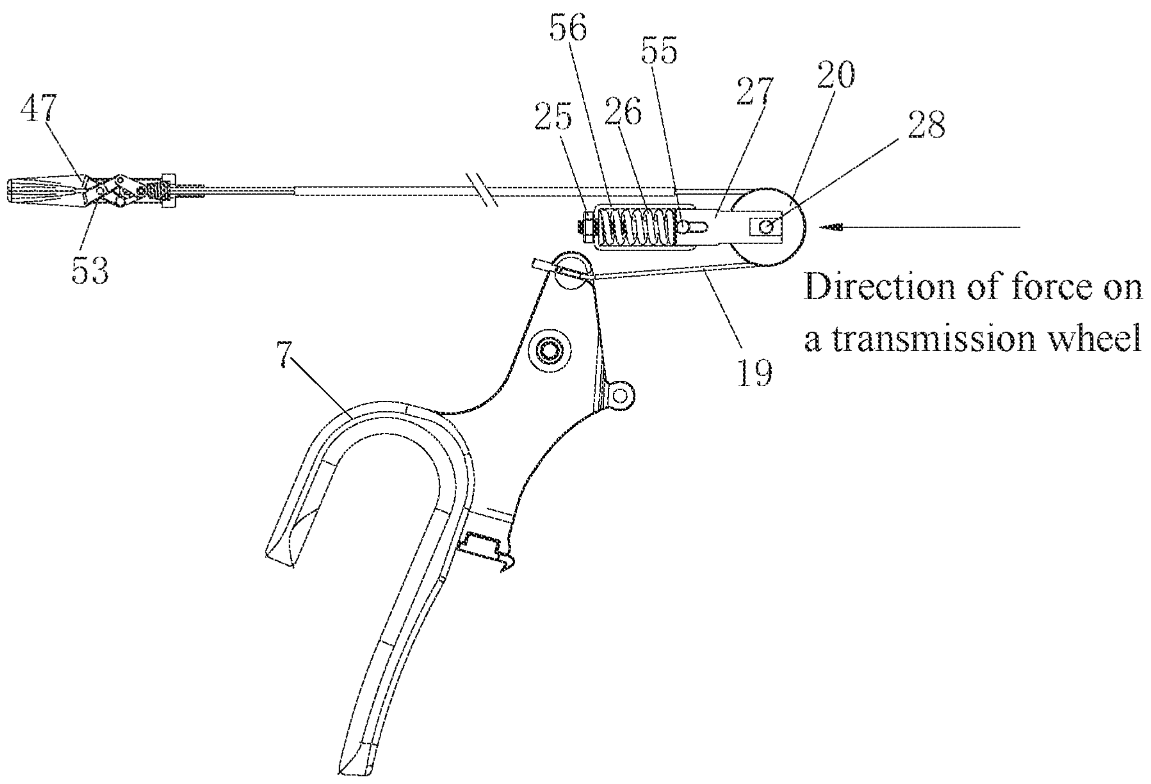
FIG. 10 is a schematic structural diagram of an unloading process of the present disclosure.

Please refer to FIGS. 4, 5, and 10. In an implementation mode, the unloading device 21 is provided in the handle body 1, and an unloading shell 56 is fixedly provided on one side of the handle body 1. A second positioning pin 55 is provided in the unloading shell 56. A movable shaft 27 is movably provided on an outer wall side of the unloading shell 56, and an unloading spring 26 is fixedly sleeved in a middle of the movable shaft 27. An adjustment nut 25 is fixedly provided on an outer wall side of a tail end of the movable shaft 27 to adjust a maximum force subjected by the surgical clamp. The transmission wheel 20 is fixedly provided at a front end of the movable shaft 27, and a second rotating shaft 28 is fixedly provided on an outer wall side of the transmission wheel 20.

The first positioning screw 9 is fixedly provided on the inner wall side of the handle body 1, and the front handle 7 is movably provided on the outer wall side of the handle body 1. The clamp head 6 is movably provided on the outer wall side of the handle body 1, and the hook 12 is fixedly provided on the inner wall side of the handle body 1. The first tension spring 10 is fixedly provided on the outer wall side of the first positioning screw 9, and is connected to the hook 12 together through the first head tension hook 69. The hook 12 is fixedly provided on the inner wall side of the handle body 1, and one end of the hook 12 is fixedly provided with the positioning column 11. The unlocking button 24 is fixedly provided in the middle of the hook 12. The second positioning screw 13 is fixedly provided on the inner wall side of the handle body 1, and the second positioning screw 13 is fixedly provided on the inner wall side of the handle body 1. The outer wall of the second positioning screw 13 is sleeved with the second tension spring 14. The second tension spring 14 is connected to the hanging hole 15 that is provided on the middle side of the front handle 7 through the second head tension hook 70. The first shaft sleeve 16 is fixedly provided on the outer wall side in a middle of the front handle 7, and the first rotating shaft 17 is movably provided in the middle of the first shaft sleeve 16. The upper end of the front handle 7 is fixedly provided with the positioning sleeve 18, which is riveted together with the first nickel titanium wire rope 19. The inner wall side of the handle body 1 is fixedly provided with the transmission wheel 20, and the first nickel titanium wire rope 19 is wound around the transmission wheel 20 and is connected to the clamp head 6. The transmission wheel 20 is movably provided on the unloading device 21. The front end of the handle body 1 is fixedly provided with the connecting sleeve 22, and the connecting sleeve 22 is connected to the second rotating device 3 through threads, the handle body 1 is movably provided with the unloading device 21 and the first rotating device 2, and the outer wall side of the front handle 7 is fixedly provided with the lock buckle 8, and the lock buckle 8 is fixed by the screw 23 that is provided at a bottom of an inner wall of the front handle 7.

In an implementation mode, the unloading spring 26 is provided in a hole of the unloading shell 56, and the movable shaft 27 passes through the unloading spring 26 and the unloading shell 56. The movable shaft 27 is locked in the unloading shell 56 through the adjustment nut 25. The second positioning pin 55 passes through the unloading shell 56 and matches with the groove position of the movable shaft 27 to prevent the movable shaft 27 from rotating. The transmission wheel 20 is provided in a recess of the movable shaft 27, and after installing the second rotating shaft 28, the second rotating shaft 28 is welded to the movable shaft 27.

The front handle 7 is closed and the first nickel titanium wire rope 19 is driven to move. The first nickel titanium wire rope 19 wraps around the transmission wheel 20 to transmit force to the upper head 47 and the lower head 53. When the upper head 47 and lower head 53 have been closed, a force is continue applied to the handle until an applied force is greater than an elastic force of the unloading spring 26. The first nickel titanium wire rope 19 pulls the transmission wheel 20 to compress the unloading spring 26, and the unloading spring 26 is contracted, thereby eliminating the force applied to the front handle 7. This ensures that the first nickel titanium wire rope 19 will not break or rivet off due to an excessive force, thereby achieving the unloading force anti-breakage function of the surgical clamp.

Figure 7:
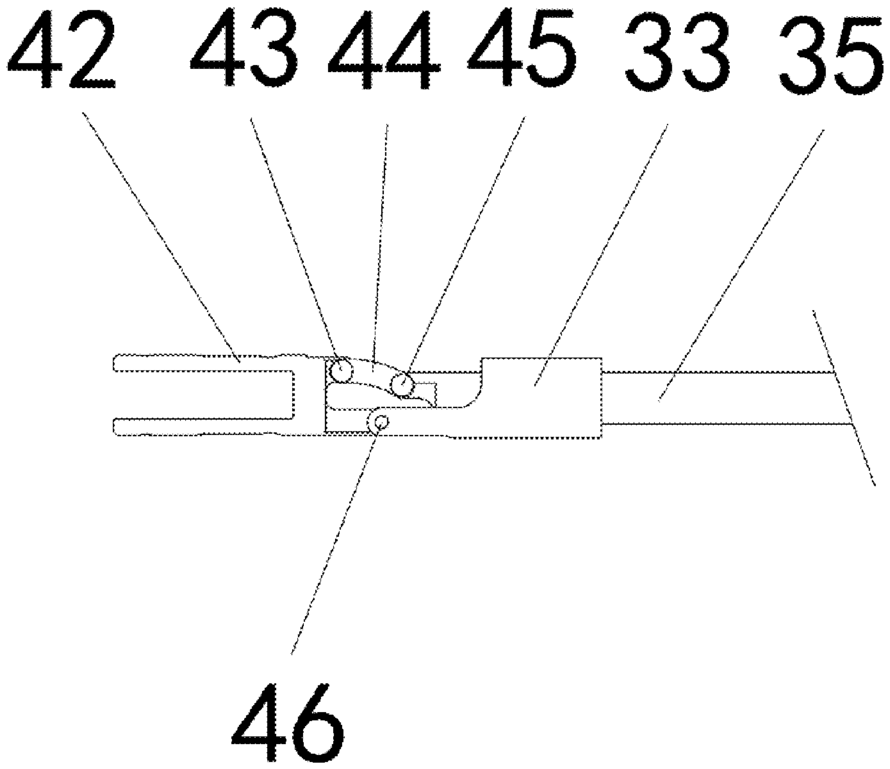
FIG. 7 is a schematic structural diagram of a swing arm of the present disclosure.
Figure 8:
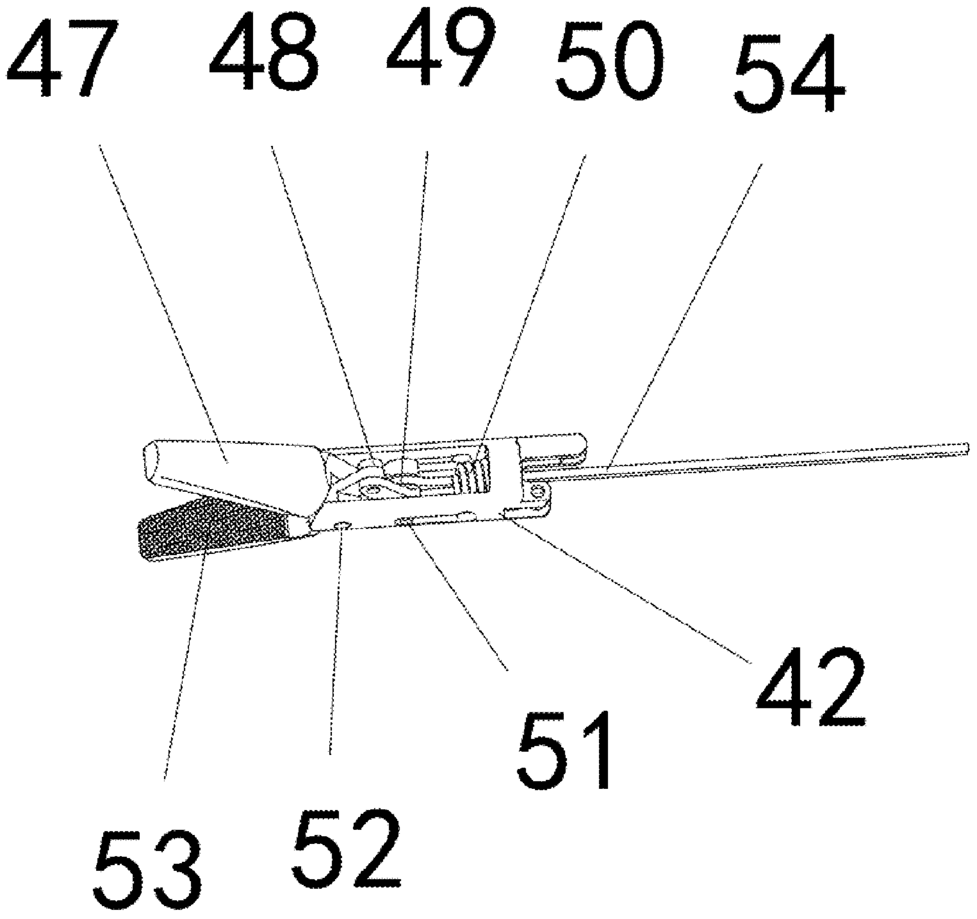
FIG. 8 is a schematic structural diagram of an upper and a lower head of the present disclosure.
Figure 9:
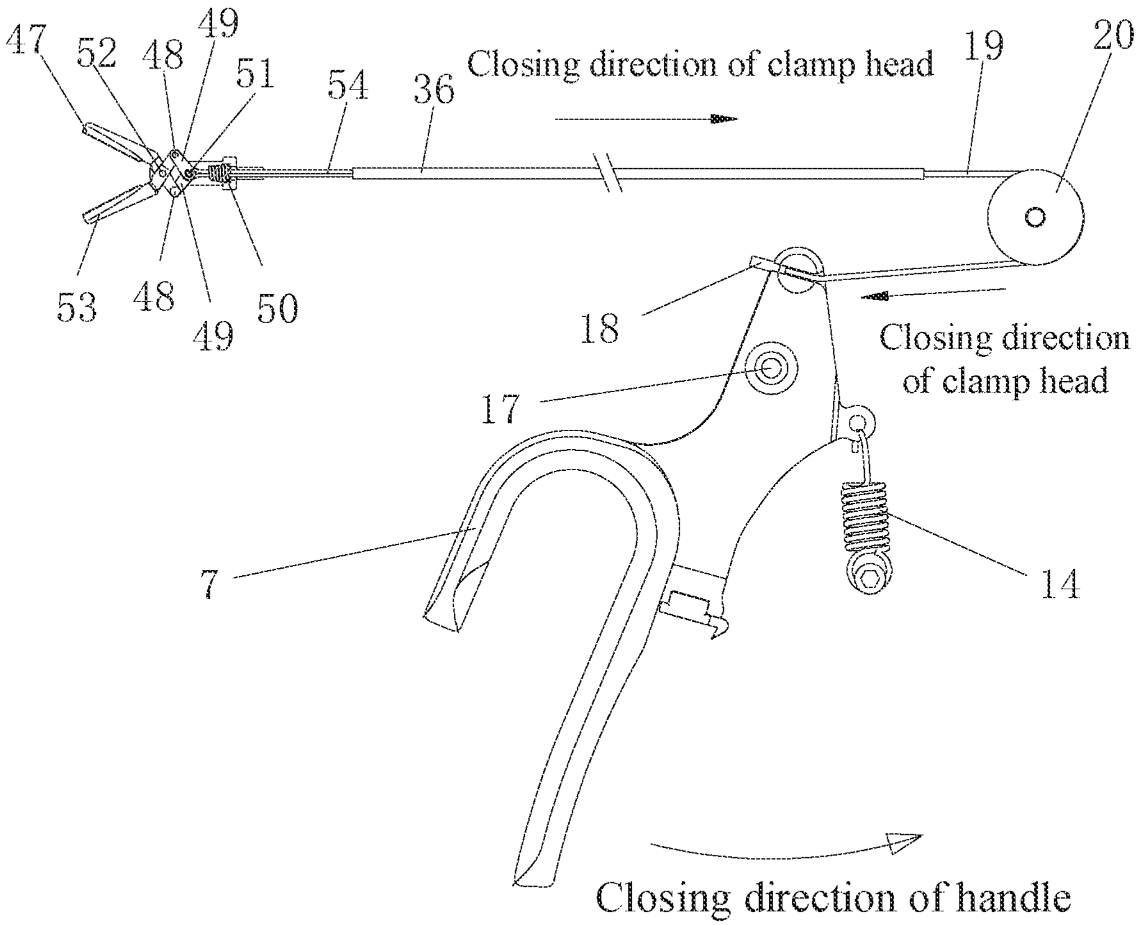
FIG. 9 is a schematic structural diagram of an opening-and-closing process of a clamp head of the present disclosure.
Figure 11:
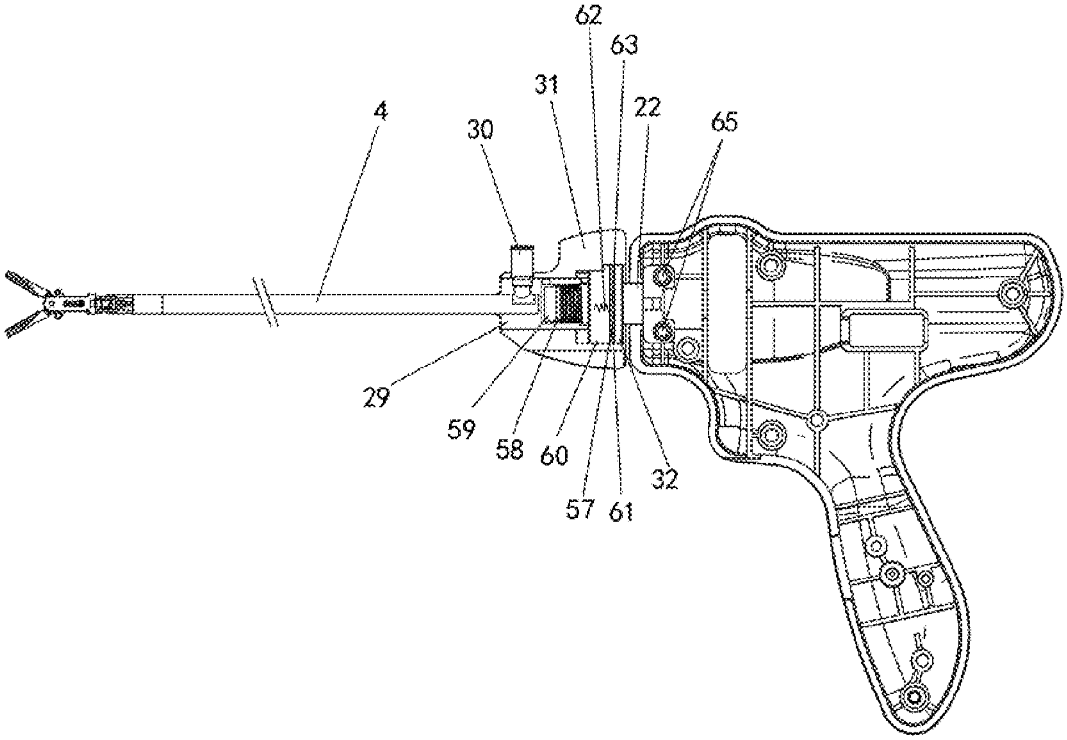
FIG. 11 is a schematic structural diagram of a rotation process of the present disclosure.
Figure 12:
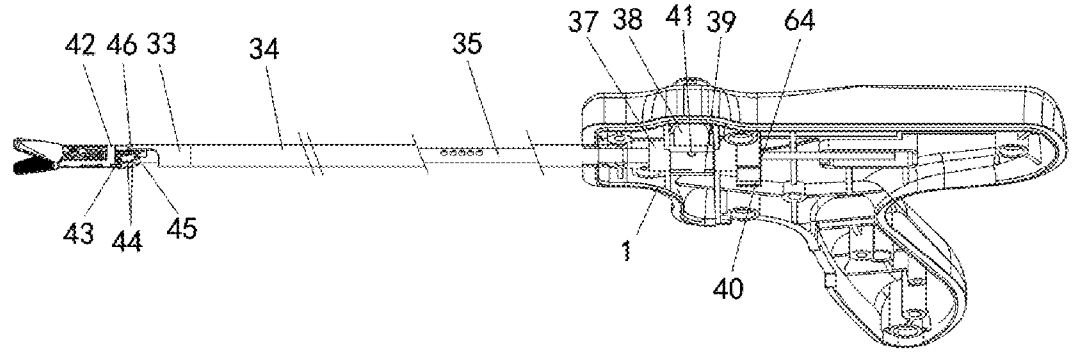
FIG. 12 is a schematic structural diagram of a swinging operation process of the present disclosure.
Figure 13:
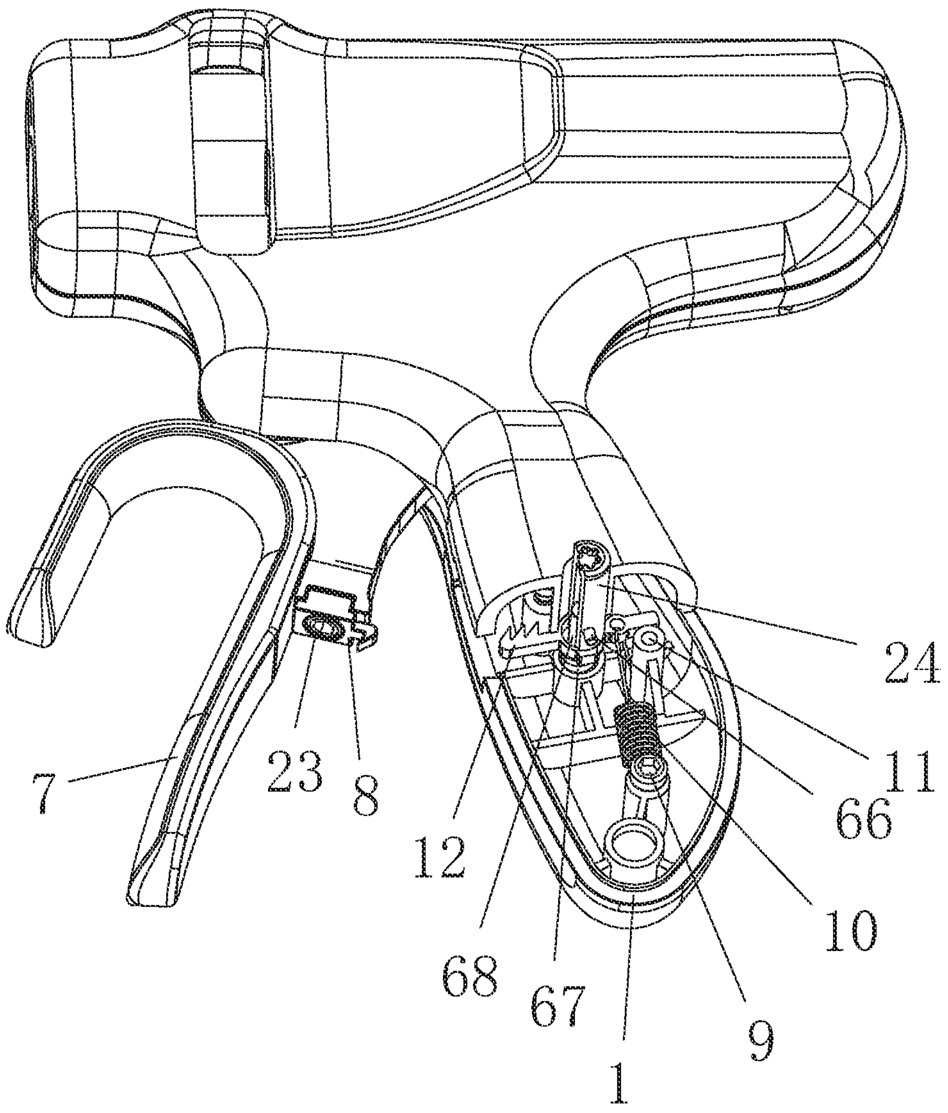
FIG. 13 is a schematic structural diagram of a locking part of a handle body of the present disclosure.

Please refer to FIGS. 4, 7, and 11. In an implementation mode, the handle body 1 is installed together with a first connecting shaft 32 in the second rotating device 3 through the connecting sleeve 22. A rubber pad 57 and a rotating component 60 are fixedly provided on an inner wall surface of the first connecting shaft 32. A copper sleeve 58 and a threaded sleeve 59 are fixedly provided at a tail end of the first connecting shaft 32. A limit pin 61 is fixedly provided below an end face of the rotating component 60. A spring 62 and a positioning steel ball 63 are fixedly provided above the rotating component 60. A rod sleeve 29 is fixedly provided on a threaded part of the rotating component 60. The rod sleeve 29 is connected to the rotating component 60 through threads. A surface of the rod sleeve 29 is sleeved with a rotating handle 31, and a flushing port 30 is fixedly provided at a front end hole of the rotating handle 31. The flushing port 30 is connected to the rod sleeve 29 and the rotating handle 31 together through threads.

In an implementation mode, the connecting sleeve 22 is provided on the handle body 1 and is fixedly through a fixing screw 65. A threaded part of the connecting sleeve 22 is sleeved with the first connecting shaft 32, and one side of the rotating component 60 is sleeved with the spring 62, the positioning steel ball 63, the limit pin 61, and the rubber pad 57. Then, it is sleeved onto the first connecting shaft 32. The threaded part of the first connecting shaft 32 is sleeved with the copper sleeve 58 and the threaded sleeve 59. The rotating component 60 is fixed on the first connecting shaft 32 and can be rotated freely around the first connecting shaft 32. The rod sleeve 29 is provided on the threaded part of the rotating component 60, and the rod body 4 is fitted into a hole of the rod sleeve 29. The rod body 4 and the rod sleeve 29 are fixed together by laser welding. The rotating handle 31 is provided on surfaces of the rod sleeve 29 and the rotating component. On the surface of the rotating component 60, a protrusion of the rotating handle 31 is matched with a recess on the surface of the rotating component 60. The flushing port 30 is inserted into the hole of the rotating handle 31 and threaded into the rod sleeve 29, the rotating handle 31 and the rod sleeve 29 are fixed together.

When the rotating handle 31 is rotated with hands, the rotating handle 31 drives the rotating component 60 to rotate together with the rod sleeve 29. As the rod body 4 is welded to the rod sleeve 29, the rod body 4 will be rotated along with the rod sleeve 29, thus rotating with the head part. Surgical universal forceps have a 360° rotation, and compared to traditional surgical clamp, universal forceps have a larger operating range within the same channel.

Please refer to FIGS. 4, 6, 7, and 12. In an implementation mode, an outer wall side of the rod sleeve 29 in the second rotating device 3 is fixedly provided with the rod body 4 through an outer tube 34. A second connecting shaft 35 is fixedly provided in the outer tube 34, and the rope rod 36 is fixedly provided in the second connecting shaft 35. A front end of the outer tube 34 is fixedly provided with a connector 33, and the connector 33 is connected to a swinging structure 5. The first rotating device 2 is fixedly provided on a surface of a rear end of the second connecting shaft 35, and the first rotating device 2 is fixedly provided in the second connecting shaft 35 through a second shaft sleeve 64.

The first rotating device 2 is installed together with the rod body 4 in the handle body 1, and a transmission shaft 37 is fixedly provided on a surface of the second connecting shaft 35. A rotating sleeve 39 is fixedly fitted on a surface of the transmission shaft 37, and transmission pins 41 are provided in two small holes in a middle of the rotating sleeve 39. The transmission pins 41 cooperate with the spiral groove provided in a middle of the transmission shaft 37.

The connector 33 is fixedly connected to the swing arm body 42 through a third connecting pin 46. The other end of the swing arm body 42 is fixedly provided together with a connecting piece 44 and is movably connected with a first connecting pin 43. The other end of the connecting piece 44 is provided together with the second connecting shaft 35 in the rod body 4 and is movably connected with a second connecting pin 45.

In an implementation mode, the rotating sleeve 39 is provided on the surface of the transmission shaft 37, and the transmission pins 41 passes through a pin hole of the rotating sleeve 39 and matches with a spiral groove of the transmission shaft 37. A rotating wheel 38 is provided on a surface of the rotating sleeve 39, and the rotating wheel 38 and the rotating sleeve 39 are fixed together by interference fit. A sliding groove 40 at a back of the transmission shaft 37 is matched with the protrusion of the handle body 1 to ensure that the transmission shaft 37 does not rotate left and right. A tail end of the second connecting shaft 35 is placed into the hole of the transmission shaft 37, fitted into the second shaft sleeve 64, and welded together with the second connecting shaft 35. The transmission shaft 37 is fixed on the second connecting shaft 35, and the second connecting shaft 35 is installed together with the connecting piece 44 after passing through the connector 33 and is connected through the second connecting pin 45. The second connecting pin 45 is welded to one side of the connecting piece 44, and the other end of the connecting piece 44 is installed together with the swing arm body 42. The first connecting pin 43 is welded to the side of the connecting piece 44, and the other end of the swing arm body 42 is assembled with the connector 33, and is connected through the third connecting pin 46; two ends of the third connecting pin 46 are welded to a hole of the connector 33. The connector 33 is welded to the outer tube 34.

The rotating wheel 38 is rotated, and the rotating sleeve 39 and the transmission pins 41 are rotated together. The transmission pins 41 and a rotating groove inside the transmission shaft 37 cooperate with each other, the transmission shaft 37 and the second connecting shaft 35 that is fixed on the transmission shaft 37 are driven to move forward and backward. The second connecting shaft 35 is moved forward, the swing arm body 42 is pushed to swing to right, and the second connecting shaft 35 is moved backward, the swing arm body 42 is pushed to swing to left, thus achieving left and right swing function of the universal forceps. Universal forceps can achieve a swing of ≥50° in left and right direction. Compared with traditional surgical clamp, universal forceps effectively solve problems of narrow working channels, large lesion areas, and the need for multiple holes to complete surgery in traditional forceps.

Please refer to FIGS. 5, 6, 8, and 13. In an implementation mode, the inner wall side of the handle body 1 is fixedly provided with the first positioning screw 9, the outer wall side of the handle body 1 is movably provided with the front handle 7, the clamp head 6 is movably provided on the outer wall side of the handle body 1; the hook 12 is fixedly provided on the inner wall side of the handle body 1, and the first tension spring 10 is fixedly provided on the outer wall side of the first positioning screw 9. The first tension spring 10 is connected to the hook 12 through the first head tension hook 69, and the hook 12 is fixedly provided on the inner wall side of the handle body 1. One end of the hook 12 is fixedly provided with the positioning column 11. The unlocking button 24 is fixedly provided in the middle of the hook 12, and the second positioning screw 13 is fixedly provided on the inner wall side of the handle body 1. The outer wall of the second positioning screw 13 is provided with the second tension spring 14, and the second tension spring 14 is connected to the hanging hole 15 that is provided on the middle side of the front handle 7 through the second head tension hook 70. The first shaft sleeve 16 is fixedly provided on the outer wall side in the middle of the front handle 7, and the first rotating shaft 17 is movably provided in the middle of the first shaft sleeve 16. The upper end of the front handle 7 is fixedly provided with the positioning sleeve 18, and the positioning sleeve 18 is riveted to the first nickel titanium wire rope 19. The inner wall side of the handle body 1 is fixedly provided with the transmission wheel 20, and the first nickel titanium wire rope 19 is wound around the transmission wheel 20 and then is connected to the clamp head 6. The transmission wheel 20 is movably provided on the unloading device 21. The front end of the handle body 1 is fixedly provided with the connecting sleeve 22, and the connecting sleeve 22 is connected to the second rotating device 3 through threads.

The handle body 1 is movably provided with the unloading device 21 and the first rotating device 2. The outer wall side of the front handle 7 is fixedly provided with the lock buckle 8, and the lock buckle 8 is fixed by the screw 23 that is provided at a bottom of the inner wall of the front handle 7.

The handle body 1 is installed together with the first connecting shaft 32 in the second rotating device 3 through the connecting sleeve 22. The inner wall surface of the first connecting shaft 32 is fixedly provided with the rubber pad 57 and the rotating component 60. The tail end of the first connecting shaft 32 is fixedly provided with the copper sleeve 58 and the threaded sleeve 59. The limit pin 61 is fixedly provided below the end face of the rotating component 60. The spring 62 and the positioning steel ball 63 are fixedly provided above the rotating component 60. The threaded part of the rotating component 60 is fixedly provided with the rod sleeve 29, and the rod sleeve 29 is connected to the rotating component 60 through threads. The surface of the rod sleeve 29 is sleeved with the rotating handle 31, and the flushing port 30 is fixedly provided at a front hole position of the rotating handle 31. The flushing port 30 is connected to the rod sleeve 29 and the rotating handle 31 through threads.

One side of the handle body 1 is provided with a central column 68, and the central column 68 is fastened to one side of the handle body 1 through interference fit. A surface of the central column 68 is provided with a reset spring 67, and an upper end of the reset spring 67 is provided with the hook 12. An upper surface of the hook 12 is provided with the unlocking button 24, and a circular hole on one side of the unlocking button 24 is fitted with a locking pin 66, and the locking pin 66 is fixed to the unlocking button 24 by welding.

In implementation mode, a recess position of the front handle 7 is provided with the lock buckle 8 and is connected through the screw 23. One side of the handle body 1 is provided with the central column 68, and the central column 68 is fastened to one side of the handle body 1 through interference fit. The surface of the central column 68 is provided with the reset spring 67, and the upper end of the reset spring 67 is provided with the hook 12. An upper end of the hook 12 is provided with the unlocking button 24, and a circular hole on one side of the unlocking button 24 is sleeved with the locking pin 66. The locking pin 66 is fixed to the unlocking button 24 by welding. The first tension spring 10 is hung at a circular hole position behind the hook 12, and the other end of the first tension spring 10 is hung on the first positioning screw 9. The positioning column 11 on one side of the handle body 1 ensures that the hook 12 is in the same position under unlocking state.

The front handle 7 is closed to drive the lock buckle 8 to mesh with the hook 12, thereby achieving self-locking function. The hook 12 has three teeth for adjusting a meshing force. When unlocking is needed, the unlocking button 24 is pressed, and the unlocking button 24 pushes the hook 12 to move downwards. A tooth profile on the hook 12 is offset from that of the lock buckle 8. The handle automatically opens under a tension of the second tension spring 14, and the unlocking button 24 pops up and returns to its original state, thus achieving the unlocking function. When the clamp does not require the locking function, a screwdriver can be used to press the unlocking button 24 and it is rotated 180°. The locking pin 66 on the unlocking button 24 is stuck on the side of the handle body 1, rendering it impossible for the unlocking button 24 to rebound. The hook 12 is in a staggered position respect with the lock buckle 8 due to the inability of the unlocking button 24 to rebound. Before closing the front handle 7, the lock buckle 8 and the hook 12 cannot engage, thus achieving a failure of the locking function.

A surface of the second rotating device 3 of the clamp is provided with the flushing port. After using the clamp, the flushing port 30 is rinsed, and water flow will flow into an interior of the clamp along the flushing port 30, thereby cleaning the clamp.

Working principle: the front handle 7 is pressed, and the front handle 7 is moved around the first rotating shaft 17. The front handle 7 pulls the first nickel titanium wire rope 19, and the first nickel titanium wire rope 19 drives the rope rod 36 and the second nickel titanium wire rope 54 to move together. The second nickel titanium wire rope 54 pulls the transmission pin shaft 51, and the transmission pin shaft 51 pulls the transmission plate 49 to move. The transmission plate 49 pulls the upper head 47 and the lower head 53 to close. When the handle is released, the return spring 50 pushes the transmission pin shaft 51 back to its original position, the upper head 47 and lower head 53 are in an open state again. The second tension spring 14 pulls the front handle 7 back to its original position, thereby achieving the opening and closing function of the surgical clamp. The lock buckle 8 cooperates with the hook 12 to achieve self-locking function of the surgical clamp.

A contraction of the unloading spring 26 eliminates the force applied to the front handle 7, thereby ensuring that the first nickel titanium wire rope 19 will not break or rivet off due to the excessive force. When the rotating handle 31 is rotated with hands, the rotating handle 31 drives the rotating component 60 to rotate together with the rod sleeve 29. As the rod body 4 is welded to the rod sleeve 29, the rod body 4 will be rotated along with the rod sleeve 29, thus rotating with its head part. The surgical universal forceps have a 360° rotation, which allows for a larger operating range within the same channel compared to traditional surgical clamp.

The rotating wheel 38 is rotated, and the rotating sleeve 39 and the transmission pins 41 are rotated together. The transmission pins 41 and the rotating groove in the transmission shaft 37 cooperate with each other, the transmission shaft 37 and the second connecting shaft 35 that is fixed on the transmission shaft 37 are driven to move forward and backward. The second connecting shaft 35 is moved forward, the swing arm body 42 is pushed to swing to right, and the second connecting shaft 35 is moved backward, the swing arm body 42 is pushed to swing to left, thus achieving the left and right swing function of the universal forceps. The universal forceps can achieve a swing of ≥50° in the left and right directions. Compared with traditional surgical clamp, universal forceps effectively solve problems of narrow working channels, large lesion areas, and the need for multiple holes to complete surgery in traditional forceps.

For those skilled in the art, it is obvious that the present disclosure is not limited to the details of the exemplary embodiments described above, and can be implemented in other specific forms without departing from the spirit or essential features of the present disclosure. Therefore, from any point of view, the embodiments should be regarded as exemplary and non-limiting, and the scope of the present disclosure is limited by the appended claims rather than the above description. Therefore, it is intended to encompass all variations falling within the meaning and scope of the equivalent elements of the claims within the scope of the present disclosure. Any reference numerals in the claims should not be regarded as limiting the claims involved.

What is claimed is:

1. An anti-breakage self-locking universal surgical clamp, comprising a handle body (1), a hook (12), a first nickel titanium wire rope (19), a front handle (7), and a clamp head (6), wherein an inner wall side of the handle body (1) is fixedly provided with a first positioning screw (9), an outer wall side of the handle body (1) is movably provided with the front handle (7) and the clamp head (6), the inner wall side of the handle body (1) is fixedly provided with the hook (12), an outer wall side of the first positioning screw (9) is fixedly provided with a first tension spring (10), and the first tension spring (10) is connected to the hook (12) through a first head tension hook 69), the hook (12) is fixedly provided on the inner wall side of the handle body (1), one side of the hook (12) is fixedly provided with a positioning column (11), and an unlocking button (24) is fixedly provided in a middle of the hook (12);

a second positioning screw (13) is fixedly provided on the inner wall side of the handle body (1), a second tension spring (14) is sleeved on an outer wall side of the second positioning screw (13);

the second tension spring (14) is connected to a hanging hole (15) provided on a middle side of the front handle (7) through a second head tension hook (70);

a first shaft sleeve (16) is fixedly provided on a middle outer wall side of the front handle (7), and a first rotating shaft (17) is movably provided in a middle of the first shaft sleeve (16);

a positioning sleeve (18) is fixedly provided on an upper end of the front handle (7), the positioning sleeve (18) is riveted together with the first nickel titanium wire rope (19), a transmission wheel (20) is fixedly provided on the inner wall side of the handle body (1);

the first nickel titanium wire rope (19) is connected to the clamp head (6) around the transmission wheel (20), the transmission wheel (20) is movably provided on an unloading device (21);

a front end of the handle body (1) is fixedly provided with a connecting sleeve (22), and the connecting sleeve (22) is connected to a second rotating device (3) through threads;

the unloading device (21) and a first rotating device (2) are movably provided in the handle body (1);

an outer wall side of the front handle (7) is fixedly provided with a lock buckle (8), and the lock buckle (8) is fixed by a screw (23) that is fixedly provided at a bottom of an inner wall of the front handle (7);

wherein the unloading device (21) comprises an unloading shell (56), a second positioning pin (55) provided in the unloading shell (56), a movable shaft (27) movably provided on an outer wall side of the unloading shell (56), an unloading spring (26) fixedly provided in a middle of the movable shaft (27), and an adjustment nut (25) fixedly provided on an outer wall side of a tail end of the movable shaft (27) to adjust a maximum force subjected by the surgical clamp:

wherein the transmission wheel (20) is fixedly provided at a front end of the movable shaft (27), and a second rotating shaft (28) is fixedly provided on an outer wall side of the transmission wheel (20) in order to support rotation of the transmission wheel (20).

2. The anti-breakage self-locking universal surgical clamp according to claim 1, wherein the unloading device (21) is provided in the handle body (1), one side of the handle body (1) is fixedly provided with the unloading shell (56).

3. The anti-breakage self-locking universal surgical clamp according to claim 1, wherein the handle body (1) is installed with a first connecting shaft (32) in the second rotating device (3) together through the connecting sleeve (22), a rubber pad (57) and a rotating component (60) are fixedly provided on an inner wall side of the first connecting shaft (32), a copper sleeve (58) and a threaded sleeve (59) are fixedly provided at a tail end of the first connecting shaft (32), a limit pin (61) is fixedly provided below an end face of the rotating component (60), a spring (62) and a positioning steel ball (63) are fixedly provided above the rotating component (60), a threaded part of the rotating component (60) is fixedly provided with a rod sleeve (29), and the rod sleeve (29) is connected to the rotating component (60) through threads;

a surface of the rod sleeve (29) is sleeved with a rotating handle (31), a flushing port (30) is fixedly provided at a front hole position of the rotating handle (31), the flushing port (30) is connected to the rod sleeve (29) and the rotating handle (31) together through threads;

an inner wall of the connecting sleeve (22) is provided with a fixing screw (65).

4. The anti-breakage self-locking universal surgical clamp according to claim 3, wherein an outer wall side of the rod sleeve (29) in the second rotating device (3) is fixedly provided with a rod body (4) through an outer tube (34), a second connecting shaft (35) is fixedly provided in the outer tube (34), an interior of the second connecting shaft (35) is fixedly sleeved with a rope rod (36), a connector (33) is fixedly provided at a front end of the outer tube (34), and the connector (33) is connected to a swinging structure (5) together;

the first rotating device (2) is fixedly provided on a surface of a tail end of the second connecting shaft (35), and a second shaft sleeve (64) is configured to fix the first rotating device (2) inside the second connecting shaft (35).

5. The anti-breakage self-locking universal surgical clamp according to claim 4, wherein the first rotating device (2) is provided with the rod body (4) in the handle body (1) together, a transmission shaft (37) is fixedly provided on a surface of the second connecting shaft (35), a surface of the transmission shaft (37) is fixedly sleeved with a rotating sleeve (39), and transmission pins (41) are provided in two small holes in a middle of the rotating sleeve (39), the transmission pins (41) cooperate with a spiral groove that is provided in a middle of the transmission shaft (37).

6. The anti-breakage self-locking universal surgical clamp according to claim 5, wherein a surface of the rotating sleeve (39) is fixedly provided with a rotating wheel (38), a tail end of the transmission shaft (37) is fixedly provided with a sliding groove (40), one side of the handle body (1) is provided with a central column (68), and the central column (68) is fastened to the one side of the handle body (1) through an interference fit, a surface of the central column (68) is provided with a reset spring (67), an upper end of the reset spring (67) is provided with the hook (12), an upper surface of the hook (12) is provided with the unlocking button (24), a circular hole on one side of the unlocking button (24) is provided with a locking pin (66), and the locking pin (66) is fixed above the unlocking button (24) by welding.

7. The anti-breakage self-locking universal surgical clamp according to claim 4, wherein the connector (33) is fixedly connected to a swing arm body (42) through a third connecting pin (46), another end of the swing arm body (42) is fixedly installed with a connecting piece (44) together, and is movably connected with a first connecting pin (43), another end of the connecting piece (44) is installed with the second connecting shaft (35) in the rod body (4) together, and is movably connected with a second connecting pin (45).

8. The anti-breakage self-locking universal surgical clamp according to claim 7, wherein a front end of the clamp head (6) is fixedly provided with an upper head (47) and a lower head (53), transmission plates (49) are respectively provided in inner wall sides of the upper head (47) and the lower head (53), and the transmission plates (49) are connected by first positioning pins (48), other ends of the transmission plates (49) are fixedly connected to a transmission pin shaft (51), and the transmission pin shaft (51) is installed on the swing arm body (42).

9. The anti-breakage self-locking universal surgical clamp according to claim 8, wherein a second nickel titanium wire rope (54) is provided in a middle of the transmission pin shaft (51), and a return spring (50) is sleeved on a surface of the second nickel titanium wire rope (54), the return spring (50) is provided in a groove of the swing arm body (42).

10. The anti-breakage self-locking universal surgical clamp according to claim 8, wherein the upper head (47) and the lower head (53) are merged and installed on the swing arm body (42), the upper head (47) and the lower head (53) are fixedly connected with a fourth connecting pin (52).

* * * * *